United States Patent [19]
McDowell

[11] Patent Number: 5,273,690
[45] Date of Patent: Dec. 28, 1993

[54] AIR-FRESHENER DEVICE EMPLOYING FORCED AIR

[76] Inventor: John L. McDowell, 10831 Roycroft St., #55, Sun Valley, Calif. 91352

[21] Appl. No.: 901,952

[22] Filed: Jun. 22, 1992

[51] Int. Cl.$^5$ ............................................. A61L 9/12
[52] U.S. Cl. ............................ 261/107; D23/368; D23/369; 428/905; 206/532; 261/DIG. 65; 422/124
[58] Field of Search ........................ D23/366–369; 428/905; 206/531, 532; 383/200; 261/DIG. 65, 107; 422/124

[56] References Cited

U.S. PATENT DOCUMENTS

| | | | |
|---|---|---|---|
| D. 288,713 | 3/1987 | Dameal | D23/366 |
| 1,769,409 | 7/1930 | Armstrong | D23/368 |
| 2,329,360 | 9/1943 | Salfisberg | 383/200 |
| 2,460,335 | 2/1949 | Buss | 261/DIG. 65 |
| 2,760,630 | 8/1956 | Lakso | 383/200 |
| 3,343,664 | 9/1967 | Poitras | 383/200 |
| 3,540,579 | 11/1970 | Hellstrom | 206/530 |
| 4,161,284 | 7/1979 | Rattan | D23/366 |
| 4,208,012 | 6/1980 | Dutcher | 261/DIG. 65 |
| 4,243,224 | 1/1981 | Spector | 428/905 |
| 4,277,024 | 7/1981 | Spector | 428/905 |
| 4,283,011 | 8/1981 | Spector | D23/367 |
| 4,305,502 | 12/1981 | Gregory et al. | 206/532 |
| 4,558,820 | 12/1985 | Harris, Jr. | D23/366 |
| 4,563,333 | 1/1986 | Frigon | D23/368 |
| 5,087,273 | 2/1992 | Ward | 261/DIG. 65 |

FOREIGN PATENT DOCUMENTS

| | | | |
|---|---|---|---|
| 1319723 | 6/1973 | United Kingdom | 206/532 |
| 2223001 | 3/1990 | United Kingdom | 206/532 |

OTHER PUBLICATIONS

U.S. application Ser. No. 206,498, Nicolle, published May 18, 1943 by A.P.C.

Primary Examiner—Tim Miles
Attorney, Agent, or Firm—Roger A. Marrs

[57] ABSTRACT

An air freshener device is disclosed herein in combination with a forced air source and which has a carrier with a plurality of fragrance or scented emitting ingredients or the like arranged in separate spaced-apart cells or compartments in rows and/or columns. The carrier includes breakable walls for each cell or compartment adapted to release the stored ingredient into a stream of oncoming forced air. Attachment elements secure the carrier to supporting structure so that released ingredient will enter the stream of forced air for distribution throughout a room.

6 Claims, 2 Drawing Sheets

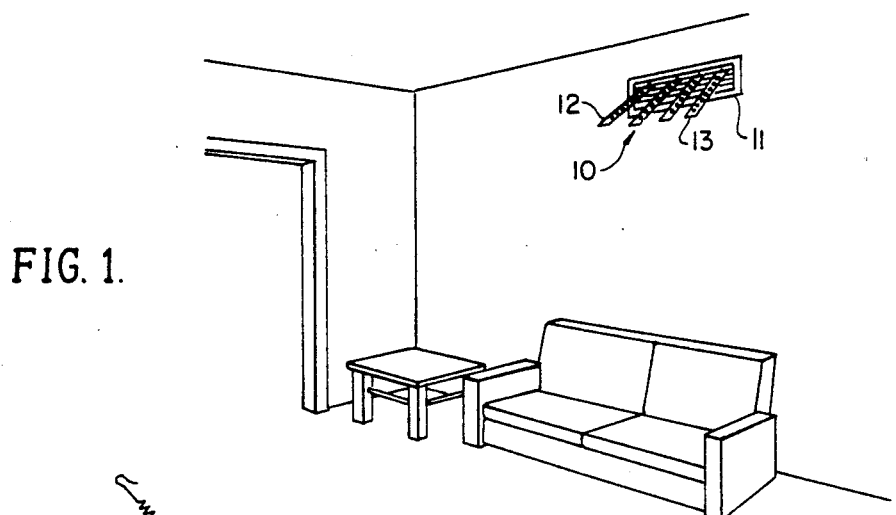
FIG. 1.
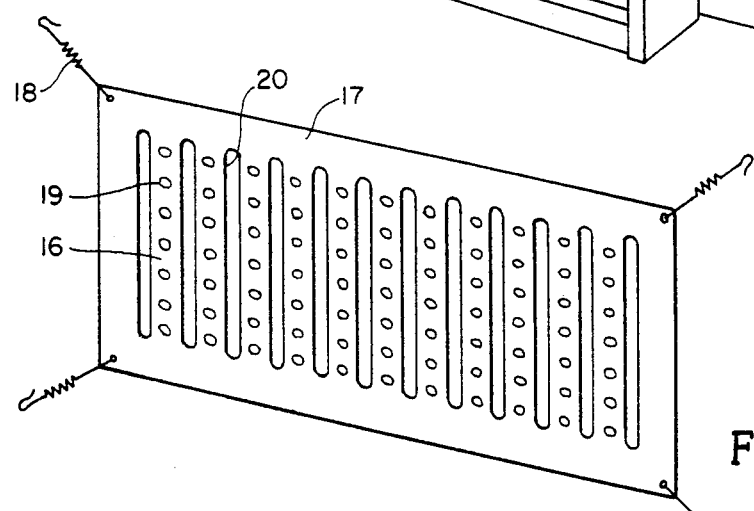
FIG. 3.
FIG. 2.
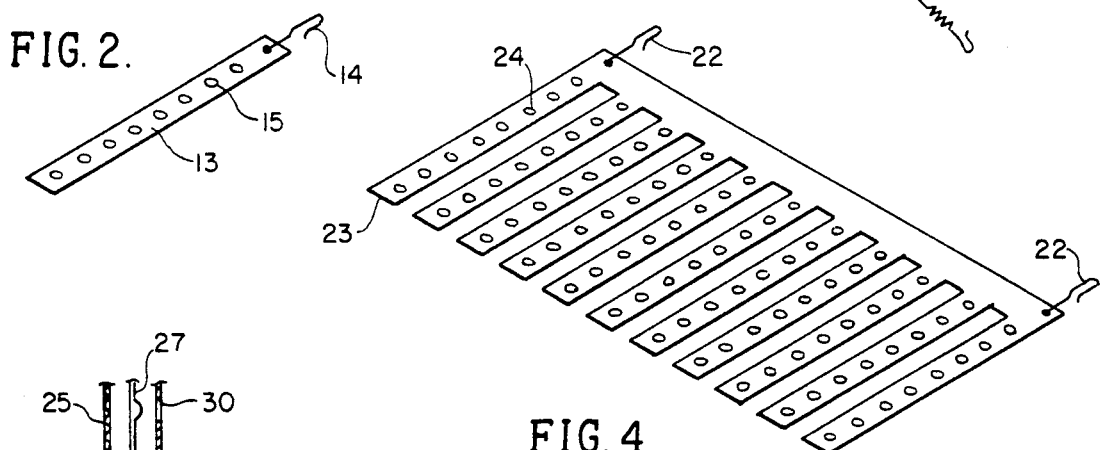
FIG. 4.
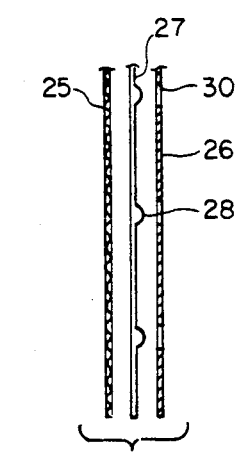
FIG. 5.

AIR-FRESHENER DEVICE EMPLOYING FORCED AIR

BACKGROUND OF THE INVENTION

1. Field of the Invention

The present invention relates to the field of room air fresheners, and more particularly to a novel air freshening apparatus having a plurality of compartments releasably storing a fragrance or scented product in a breakable cell and which is employed in combination with a source of forced air in order to distribute released product throughout a predetermined area.

2. Brief Description of the Prior Art

In the past, it has been the conventional practice to employ room air fresheners which employ sponge or matrix-like material containing a scented product or ingredient which is released into the surrounding air as the product is suspended by a string, hook or the like from a support. Such prior devices are shown in U.S. Pat. Nos. 4,889,286 and 4,931,224. Although such devices have been proven useful to release a scented ingredient or product, difficulties and problems have been encountered in distributing the released product throughout a specified area, such as a room. Once released, no means is provided for such distribution other than ambient wind or air currents which randomly enter the room or specific area. Although attempts have been made to provide distribution through the use of spray cans or the like which use a pressurized substance for forcing the fragrance ingredient from the can, such a procedure and device requires that the ingredient be mixed with the pressurized substance and that expulsion from the container be made by the user through a nozzle. Such a device does not take advantage of existing forced air sources already installed in a room and requires the user to purchase the can, nozzle and the pressurized substance for forcing the fragrance from the container which is expensive and requires disposal after use.

Therefore, a long-standing need has existed to provide a novel air freshening system which eliminates the odors and distributes pleasant fragrances into a room with the assistance of an air conditioning system employing the inherent forced air in such system. Such a novel air freshening system should combine the instant-freshening characteristic of spray can usage with the long-lasting fragrance distribution of a separate plug-in and wick type products which have been conventionally used.

SUMMARY OF THE INVENTION

Accordingly, the above problems and difficulties are obviated by the present invention which provides a novel air freshening system which employs a carrier having a plurality of storing cells or compartments for holding a product or ingredient, such as air freshener or the like, between breakable sidewalls which includes means for detachably connecting the carrier to a source of forced air. Upon release of the scent or fragrance ingredient within the cell, the forced air will mix with and carry the fragrant ingredient for distribution throughout a room.

Therefore, it is among the primary objects of the present invention to provide a novel air freshening system having releasable fragrant or scent ingredients carried in breakable pods or cells which will readily be introduced into a forced air stream for distribution throughout a room.

Another object of the present invention is to provide a novel air freshening system wherein the fragrance or scent ingredient is not previously mixed with a pressurized source and wherein the ingredient is separate from the pressurized source until the ingredient is released by the user for mixing with the forced air and for distribution thereby.

Another object of the present invention is to provide a novel system for releasing a flowable product into a forced air stream system that is detachably connected to the system in alignment with the stream of forced air so that when released, mixture occurs and the forced air will carry the ingredient into the surrounding area.

A further object of the present invention is to provide an air freshening system having a plurality of breakable cells arranged in rows and columns across the frontal area of a forced air distribution system and wherein selected release of the ingredient from the cells mixes with the stream of forced air for delivery and distribution throughout a room.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is a front perspective view of a typical area intended to receive the air freshening ingredient and illustrates a forced air system having the air freshener carrier of the present invention incorporated therewith;

FIG. 2 is a front perspective view of a strip serving as a carrier having a plurality of cells storing fragrant product or the like;

FIG. 3 is another version of the present invention illustrating a plurality of breakable cells arranged in parallel rows along the length of a carrier for attachment to the supply of forced air;

FIG. 4 is a perspective view similar to the device of FIG. 3 wherein the breakable cells are arranged in flexible strips along the length of the carrier;

FIG. 5 is an enlarged transverse cross-sectional of a typical carrier illustrating the breakable cells arranged between supporting fabric layers;

DESCRIPTION OF THE PREFERRED EMBODIMENT

Figure 6:
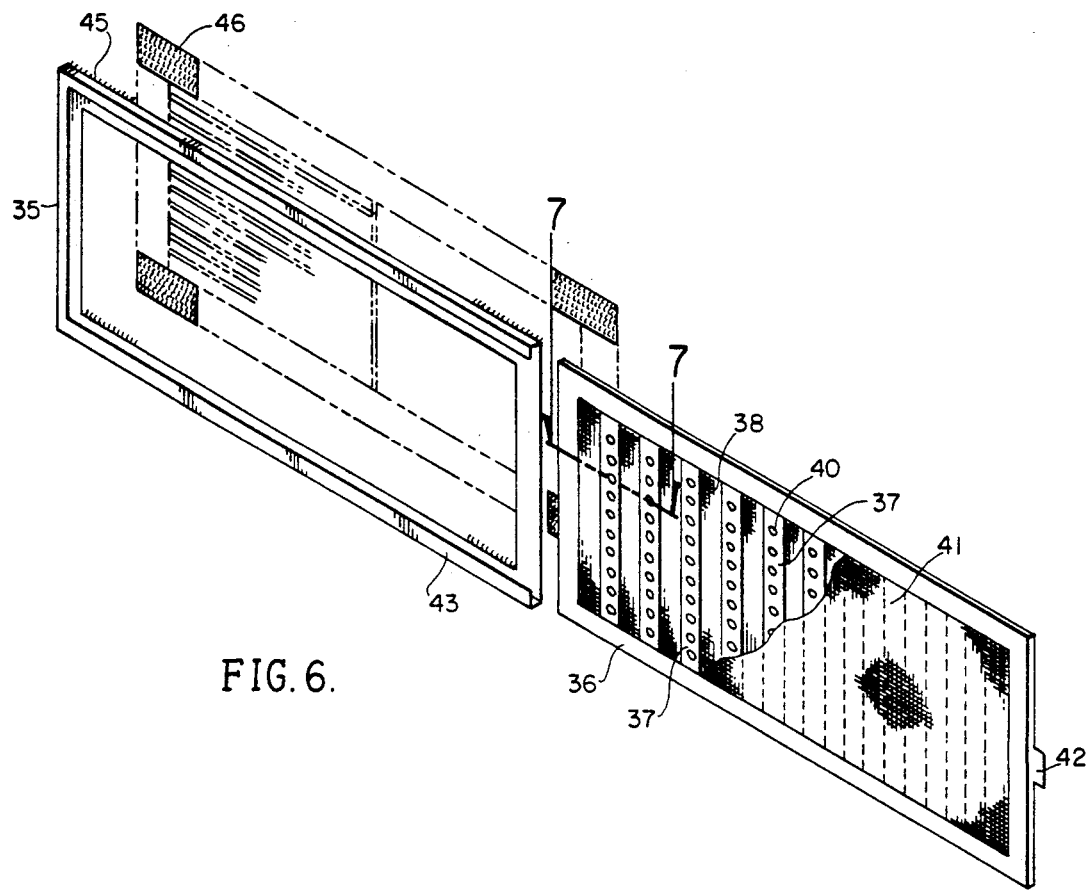
FIG. 6 is an exploded perspective view showing another version of the present invention.

Referring to FIG. 1, a typical room is illustrated in which a forced air system is employed to distribute and introduce fresh air into the room area. The forced air is discharged through a vent 11 and is included with the air freshening apparatus in combination and is represented in general by the arrow 10. Numeral 12 indicates the air freshening apparatus and it can be seen that as the freshener ingredient or substance is released into the air exiting from the vent 11, the air conditioned with the freshener will circulate about the room.

Referring to FIG. 2, one version of the air freshener apparatus is illustrated wherein a carrier takes the form of a strip 13 which is elongated and composed of flexible material so that when it is hooked to the vent 11 by means of fastener 14, the carrier strip will wave when the forced air system is in operation. A plurality of breakable cells, such as indicated by numeral 15, are provided in a row along the length of the strip 13 and a suitable product or ingredient is encapsulated within each cell for release when the walls of the cell are broken. It is to be understood that the substance or ingredient may take the form of an air freshening composition or other suitable substance such as a health product or the like. Also, in some instances, substances such as nail polish remover, air conditioner or the like may be carried in the respective cells for other applications.

The embodiment shown in FIG. 2 can be used individually or as shown in FIG. 1, a multiple arrangement of strips 13 can be placed at the outlet vent of the forced air system. When desired, the user may simply use his fingers to break the walls of selected cells 15 placed along the strip so that the quantity of ingredients or substance released can be controlled. Furthermore, the longevity of the strip can also be controlled by the number of cells which are broken at any one time.

Referring now in detail to FIG. 3, another version of the invention is provided wherein the carrier takes the form of a frame 17 which is rigid and may be attached to the vent 11 by corner spring hooks, such as hook 18. The frame 17 supports a plurality of strips 16 which are arranged in fixed spaced-apart parallel relationship across the face of the frame and which are separated by slots or spaces 20. When installed, the forced air discharged through the vent 11 will pass through the openings 20 and come in contact with any of the ingredients or substance released from the breakable cells which are indicated by numeral 19.

Referring now in detail to FIG. 4, another embodiment is illustrated wherein the carrier is indicated by numeral 21 which supports a plurality of strips, such as strip 23, which depend from the carrier and the strips are similar to the strip 13 in that they are flexible and will flutter in the forced air stream. Each of the respective strips includes a row of breakable cells, such as cell 24, and the assembly can be attached to the vent 11 by means of hooks 22.

Referring now in detail to FIG. 5, an enlarged view is shown of a typical strip in which outer layers 25 and 26 can be composed of a suitable fabric and may be rigidized or made flexible as desired. The inner layer is indicated by numeral 27 and this layer includes the cells, such as cell 28. Preferably and in one form, cell 28 may protrude through an opening 30 in one of the outer layers, such as layer 26. Referring further to FIG. 5, it can be seen that the inner layer 27 may be sandwiched between the outer layers 25 and 26 and securement may be by any means such as pressure, adhesive sealing or the like. The cell 28 is composed of a bubble-like sidewall which may be readily broken by the exertion of finger pressure by the user. Upon such breakage, the substance or ingredients within the cell will pass through the opening 30 into the air stream from the forced air system. In some instances, the ingredients may penetrate into the fabric outer layers so as to be retained until withdrawn by the air stream.

Figure 7:
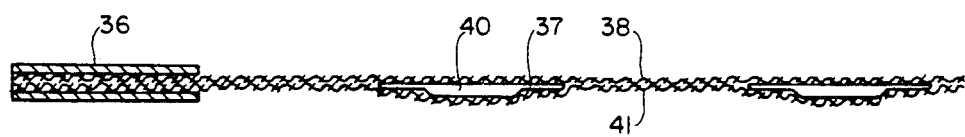
FIG. 7 is a fragmentary cross-sectional view of the carrier shown in FIG. 6 as taken in the direction of arrows 7—7 thereof.

Referring now in detail to FIGS. 6 and 7, another embodiment of the invention is shown wherein the air freshening apparatus is of a two-part construction wherein the first part is a frame 35 having a central opening which is occupied by a panel 36 so that a plurality of air freshener strips, such as strip 37, is disposed in the opening. The strips may be carried across the face of the panel 13 in spaced-apart relationship having their opposite ends secured to the panel peripheral edge and either openings may be provided between the strips or, as illustrated, a simple fabric 38 may be employed. The fabric may be useful in absorbing the fragrant substance released from the respective cells, such as cell 40 carried on strip 37. A single layer of fabric 38 may be employed as well as a second layer identified by numeral 41 which resides on the opposite side of the plurality of air freshener strips. A finger tab 42 is useful for grasping by the user so that the panel 36 may be introduced between rails 43 and 44 in order to mount the panel on the frame 35. Once the panel is so assembled, attachment of the frame and the panel to the vent 11 may be by means of a hook and pile fastener wherein the hook is represented by numeral 45 and the pile portion of the closure is indicated by numeral 46.

In view of the foregoing, it can be seen that the novel air freshener apparatus of the present invention employs the combination of an air freshener releasing device, such as the plurality of strips or an individual strip in combination with the forced air stream derived from a conventional forced air system normally installed in a dwelling. Use is also made of the conventional vent or outlet for the stream of forced air and the air freshening apparatus portion is detachably connectable to the vent to permit the air to be forced past released fragrance or scent ingredients to achieve distribution throughout the room. The device may be composed of plastic, metal, fabric or other available materials. It is to be particularly noted that aerosols are not needed and that there are no child-endangering plug-in units. The inventive system eliminates odors and distributes pleasant fragrances into the room with the aid and use of the installed forced air system or air conditioning system. The carrier with the breakable cells is a system that is attached to the conventional vents of an air conditioning or forced air system which employs the forced air to distribute the freshener throughout the room without the use of a chemical propellant. A main feature of the inventive system is that it combines the instant-freshening characteristic of conventional sprays with the long-lasting fragrance distribution of a plug-in and wick type product that are in common usage.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. In an air freshener system having an air freshener device used in combination with a forced air system, the combination which comprises:

said forced air system having a vent for discharging pressurized air into a room area;

said air freshener device having a carrier attached to said vent in a critical location to interfere with the discharging pressurized air;

said carrier having a plurality of breakable cells disposed in spaced-apart relationship along the length of said carrier; and each cell having a fragile wall structure holding a quantity of air freshener ingredients and releasable into surrounding discharging air stream in response to breakage of said fragile wall structure.

2. The invention as defined in claim 1 wherein:

said carrier is an elongated strip of flexible material having a central layer carrying said cells and outer layers supporting said central layer;

a selected one of said outer layers having openings in alignment with said cells to accommodate release of said air freshener ingredients.

3. The invention as defined in claim 1 wherein:

said carrier is a frame having a plurality of strips disposed in fixed parallel spaced-apart relationship with slots between adjacent ones of said strips.

4. The invention as defined in claim 3 including:

releasable attachment means on said carrier for mounting said carrier to said vent.

5. The invention as defined in claim 4 wherein:

said air freshener device includes a frame having a central opening; and a panel slideably disposed on said frame;

said strips being carried on said panel and disposed to occupy said frame central opening when said panel is slid onto said frame.

6. The invention as defined in claim 5 wherein:

said panel includes exterior layers of fabric separated by said plurality of strips; and said fabric layers adapted to absorb said air freshener ingredients in response to breakage of said cell fragile wall structure.

* * * * *